(12) United States Patent
Chiu

(10) Patent No.: US 8,846,740 B2
(45) Date of Patent: Sep. 30, 2014

(54) BIOTHERAPEUTICS FOR THE TREATMENT OF INFECTIOUS DISEASES

(75) Inventor: Gordon Chiu, Chatham, NJ (US)

(73) Assignee: Biological Responsibility, LLC, Austin, TX (US)

( * ) Notice: Subject to any disclaimer, the term of this patent is extended or adjusted under 35 U.S.C. 154(b) by 0 days.

(21) Appl. No.: 13/343,066

(22) Filed: Jan. 4, 2012

(65) Prior Publication Data

US 2012/0172342 A1 Jul. 5, 2012

Related U.S. Application Data

(60) Provisional application No. 61/429,664, filed on Jan. 4, 2011.

(51) Int. Cl.
| | |
|---|---|
| *A61K 9/06* | (2006.01) |
| *A61K 47/44* | (2006.01) |
| *A61L 15/24* | (2006.01) |
| *A61L 15/60* | (2006.01) |
| *A61L 26/00* | (2006.01) |
| *A61K 9/00* | (2006.01) |
| *A61F 13/00* | (2006.01) |
| *A61L 15/42* | (2006.01) |
| *A61L 15/44* | (2006.01) |
| *A61K 47/34* | (2006.01) |
| *A61K 9/70* | (2006.01) |

(52) U.S. Cl.
CPC . *A61K 9/06* (2013.01); *A61K 47/44* (2013.01); *A61K 13/0233* (2013.01); *A61K 9/7007* (2013.01); *A61L 15/60* (2013.01); *A61L 2300/406* (2013.01); *A61L 26/0066* (2013.01); *A61K 9/0014* (2013.01); *A61L 2300/222* (2013.01); *A61L 2300/408* (2013.01); *A61L 15/24* (2013.01); *A61F 13/00063* (2013.01); *A61L 15/425* (2013.01); *A61L 26/0014* (2013.01); *A61L 26/0071* (2013.01); *A61L 15/44* (2013.01); *A61L 26/008* (2013.01); *A61K 47/34* (2013.01)
USPC ............................. 514/396; 424/445; 424/446

(58) Field of Classification Search
CPC ..... C08L 9/06; A61L 15/225; A61L 26/0009; A61L 26/0052; A61K 9/06
USPC .................................................. 424/446, 445
See application file for complete search history.

(56) References Cited

U.S. PATENT DOCUMENTS

| | | | |
|---|---|---|---|
| 3,814,097 | A | 6/1974 | Ganderton |
| 3,921,636 | A | 11/1975 | Zaffaroni |
| 3,972,995 | A | 8/1976 | Tsuk |
| 3,993,073 | A | 11/1976 | Zaffaroni |
| 3,996,934 | A | 12/1976 | Zaffaroni |
| 4,031,894 | A | 6/1977 | Urquhart et al. |
| 4,060,084 | A | 11/1977 | Chandrasekaran |
| 4,069,307 | A | 1/1978 | Higuchi |
| 4,230,105 | A | 10/1980 | Harwood |
| 4,292,299 | A | 9/1981 | Suzuki |
| 4,292,303 | A | 9/1981 | Keith et al. |
| 5,389,092 | A | 2/1995 | Guillemet |
| 6,270,792 | B1 | 8/2001 | Guillemet |
| 7,429,396 | B2 | 9/2008 | D'Amelio, Sr. et al. |
| 2002/0128345 | A1 | 9/2002 | Paul |
| 2003/0036717 | A1 | 2/2003 | Apert |
| 2005/0124724 | A1 | 6/2005 | Burton |
| 2005/0176871 | A1 | 8/2005 | Auguste |
| 2005/0228115 | A1 | 10/2005 | Auguste |
| 2006/0111485 | A1 | 5/2006 | Laghi |
| 2009/0028929 | A1 | 1/2009 | Stefanelli et al. |

FOREIGN PATENT DOCUMENTS

| | | |
|---|---|---|
| EP | 1 212 093 B1 | 7/2004 |
| WO | WO 96/23463 | 8/1996 |
| WO | WO 97/07802 A1 | 3/1997 |
| WO | WO 2004/1083226 A1 | 9/2004 |
| WO | WO 2007/1141513 A1 | 12/2007 |
| WO | WO 2010/1003197 A1 | 1/2010 |

OTHER PUBLICATIONS

PCT International Preliminary Report on Patentability; PCT/US2012/020131; Chiu, Gordon; Jul. 10, 2013.
PCT International Search Report & Written Opinion; PCT/US2012/020131; Chiu, Gordon; Jul. 13, 2012.

*Primary Examiner* — Sreeni Padmanabhan
*Assistant Examiner* — Irina Neagu
(74) *Attorney, Agent, or Firm* — Gearhart Law, LLC

(57) ABSTRACT

An occlusive dressing made with an elastomeric gel and one or more active agents is described. The elastomeric gel contains a plasticizing oil phase and a block copolymer agent. Methods of preventing, treating, curing or mitigating an infectious disease and methods of making the dressings are also disclosed.

9 Claims, No Drawings

BIOTHERAPEUTICS FOR THE TREATMENT OF INFECTIOUS DISEASES

CLAIM OF PRIORITY

This application claims the priority of U.S. Ser. No. 61/429,664 filed on Jan. 4, 2011, the contents of which are fully incorporated herein by reference.

FIELD OF THE INVENTION

The invention relates to novel treatments for infectious diseases, in particular, an occlusive dressing and methods of treatment.

BACKGROUND OF THE INVENTION

The present invention relates to novel treatments for infectious diseases, in particular, an occlusive dressing and methods of treatment.

Occurring worldwide, most fungi are largely invisible to the naked eye, living for the most part in soil, dead matter, and as symbions of plants, animals, or other fungi. However, several species of the fungi are significant pathogens of humans and other animals or crops. The most commonly known human pathogens are part of the *Candida, Aspergillus* and/or *Fusarium* species.

*Candida albicans* is among the gut flora, the many organisms which live in the human mouth and gastrointestinal tract. Under normal circumstances, *C. albicans* lives in 80% of the human population with no harmful effects, although overgrowth results in candidiasis. *Candida albicans* is a causal agent of opportunistic oral and genital infections in humans. Systemic fungal infections have emerged as important causes of morbidity and mortality in immunocompromised patients (e.g., AIDS, cancer chemotherapy, organ or bone marrow transplantation). In addition, hospital-related infections in patients not previously considered at risk (e.g. patients in an intensive care unit) have become a cause of major health concern.

Today, there are 4 classes of established antifungal drugs on the market: (1) the polyenes (e.g. amphotericin B, nystatin, natamycin), (2) the azoles (e.g. fluconazole, itraconazole, voriconazole), (3) allylamines (e.g. terbinafine), and (4) the newly introduced echinocandins (e.g. caspofungin). Of these classes, only the polyenes, azoles and echinocandins are used to treat systemic fungal infections, not the allylamines. All the currently marketed antifungal drugs have major drawbacks, including no broad-spectrum activity, no per oral absorption, side-effects, low antifungal activity, no fungicidal activity, drug-drug interactions and high costs.

Diseases in other areas, such as Human Immunodeficiency Virus/Acquired Immunodeficiency Syndrome (HIV/AIDS) and resistant bacteria such as Methacillin-resistant *Staphylococcal aureus* (MRSA) and *Staphylococcal epidermidis* (MRSE), have created multiple problems for pregnancy and intimate relationships. Furthermore, animal husbandry indicates that diseases will reduce the yield of animals for prized animals which could be devastating to limited breeding cycles in certain species.

Current delivery systems lack the ability to create high surface area contact points; therefore, recurring disease, infection and reinfections are prevalent. This rate increases for individuals with compromised immunes systems, such as those with cancer and HIV, for individuals with multiple partners or conditions that can lead to reinfection.

By utilizing the unique elastomeric matrix described herein, the end user would have increased contact areas with an extremely thin film of drug in the delivery device, thereby alerting the environment for recurring infectious diseases, preventing spread of disease and in many cases effectuating a cure by breaking the cycle of spread of disease.

There is still a stringent need in the art for potent antifungals, antibacterial and antivirals for topical or systemic infections, especially with a broad spectrum activity against multiple species, and which can readily transmit into the multiple dermal layers via creating a high surface area of contact points and thereby bring individuals to a cure.

Therefore a goal of the present invention is to satisfy this urgent need by identifying efficient and non-harmful pharmaceutically active ingredients and combinations of ingredients for the prevention and treatment of infectious diseases, especially of fungal, bacterial, viral infections and other dermal wounds and abrasions in animals and in humans.

WO 2010/003197 relates to compounds that are substituted morpholin-2-one structure and it has been shown in the present invention that they possess antifungal activity for treatment of fungal diseases, but does not utilize the delivery system of this invention, instead using polymer carriers such as for example polyesters, polyamino acids, polyvinyl pyrrolidone, ethylene-vinyl acetate copolymers, methylcellulose, carboxymethylcellulose, protamine sulfate, but not SEBS and SEPS.

U.S. Pat. Nos. 5,466,235; 5,782,818; 5,806,523; and 5,807,360 relate to a polymer which does not demonstrate application for dermal use for the delivery of medications which are anti-fungal, ant-bacterial or anti-viral.

WO 2007/141513 provides coumarin compounds, in particular glycosidic coumarin compounds, useful in the treatment of dermatophyte fungal infections.

EP 1 212 093 describes Emu Oil, an animal-derived lipid that is useful as a carrying agent for anti-microbial formulations, that are disclosed as useful components in anti-bacterial, anti-fungal, and anti-viral treatments.

Transdermal Delivery

Percutaneous or transdermal delivery of pharmacologically active agents has become feasible in recent years largely due to vehicles therefore which allow increased permeation of said agents into the body surface to which applied. Such agents which may be useful for the preparation of a xanomeline transdermal patch formulation include, but are not necessarily limited to, dimethylsulfoxide (U.S. Pat. No. 3,551,554); various 1-substituted azacycloalkan-2-ones such as azone (U.S. Pat. Nos. 4,562,075, 4,405,616, 4,326,893 and 3,989,816); sugar esters in combination with sulfoxide or phosphine oxide (U.S. Pat. Nos. 4,130,667, 4,130,643, 4,046,886, 3,952,099, and 3,896,238); lower alkyl amides (U.S. Pat. No. 3,472,931); certain aliphatic sulfoxides (U.S. Pat. No. 3,903,256); a composition containing glycerol monooleate, ethanol and isopropyl myristate (U.S. Pat. No. 4,335,115); a binary mixture of 1-dodecylazacycloheptan-2-one and a compound selected from a diol or a second N-substituted azacycloalkyl-2-one (U.S. Pat. No. 4,557,934); and polyethylene glycol monolaurate (U.S. Pat. No. 4,568,343).

A variety of devices for transdermal delivery including gelling agents, cream and ointment bases, and the like, have been described in the art. For example, such devices include, but are not limited to those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, and 4,292,303.

U.S. Pat. Nos. 3,598,122 and 3,598,123 describe silicone rubbers and hydrophilic polymers of monoesters of an olefinic acid, such as acrylic acid and methacrylic acid. Exemplary polymers of this class include poly (hydroxyethylacrylate) and poly (hydroxyethylmethacrylate).

U.S. Pat. Nos. 3,710,795, 3,731,683 and 3,742,951 describe a solid inner matrix material having drug dispersed there through surrounded by an outer polymeric membrane which includes heat shrinkable polymeric films in the form of tubes, spheres, ellipsoids, envelopes, etc.

U.S. Pat. No. 3,814,097 is a pad provided with tiny spikes. These tiny spikes augment the absorption of the drug.

U.S. Pat. No. 3,921,636 is a device which comprises a plurality of reservoirs containing drug distributed through a matrix. Especially, the invention relates to an intrauterine drug delivery device comprising a matrix of silicone elastomer having a plurality of drug reservoirs dispersed therethrough, the reservoirs comprising progesterone particles each microencapsulated within a drug release rate controlling polyethylene wall. Suitable materials permeable to the passage of drug include copolymers such as acrylonitrile/dithioglycidol, acrylonitrile/ethylene oxide, poly(vinyl butyral) comprised of 11 to 45% free hydroxyls, anisotropic permeable microporous membranes of ionically associated polyelectrolytes, the polymers formed by the coprecipitation of a polycation and a polyanion, treated aliphatic polyamides and the like; natural gums such as guar, acacia, pectins, and the like. Also, materials such as starch, regenerated cellulose, cellulose diacetate, cellulose triacetate, regenerated proteins, polyurethanes, polydinitrites, polyarylenes, and polycarbonates are disclosed.

U.S. Pat. No. 3,972,995 relates to a buccal dossage form comprising a moisture-activated adhesive precursor comprised of a hydrocolloid admixed with polyvinylpyrrolidone, water-insoluble support member comprised of a film of ethylcellulose plasticized with castor oil as well as a moisture activated adhesive precursor comprised of finely powdered Karaya gum in a viscous solution of polyvinylpyrrolidone in polyethylene glycol.

U.S. Pat. Nos. 3,996,934, 3,996,934 is a bandage comprised of a laminate of a backing member defining one face surface of a bandage and a middle reservoir containing a drug.

U.S. Pat. Nos. 4,031,894, 4,060,084, 4,060,084 and 4,201,211 is a bandage that is a four-layer laminate of a protective backing; a gelled, mineral oil-polyisobutene-scopolamine reservoir lamina that is the source of the constant dosage; a microporous membrane that controls the constant dosage rate; and a gelled, mineral oil-polyisobutene-drug adhesive layer that is the source of the pulse dose and the means by which the bandage is attached to the skin.

U.S. Pat. No. 4,069,307 is a drug-delivery device for releasing a drug at a continuous and controlled rate for a prolonged period of time is comprised of a shaped body of polymeric material containing a pharmaceutically acceptable drug and permeable to passage of the drug by diffusion. The polymeric material is an ethylene-vinyl acetate copolymer having a vinyl acetate content of about 4 to 80% by weight and a melt index of about 0.1 to 1000 grams per 10 minutes.

U.S. Pat. No. 4,077,407 relates to osmotic device for delivering an active agent which contains polymeric cellulose esters and copolymeric cellulose esters such as mono, di, and tricellulose acylates.

U.S. Pat. No. 4,230,105 is a pressure sensitive adhesive composition comprising hexane, polyvinylethylether, polyvinylethyl ether, glycerol ester of hydrogenated rosin and polyethylene glycol 400.

U.S. Pat. No. 4,292,299 relates to a slow-releasing medical preparation to be administered by adhering to a wet mucous surface, wherein the polymer of the adhesive layer is at least one polymer selected from a group comprising acrylic acids or their pharmaceutically acceptable nontoxic salts, copolymers of acrylic acid or their pharmaceutically acceptable nontoxic salts, hydrophilic vinyl copolymers not copolymerized with acrylic acid as a main component, hydrophilic cellulose derivatives, polysaccharides or their derivatives and gelatine or collagen or their derivatives with improved swellability. The polymer of the adhesive layer is a mixture of cellulose ether and polyacrylic acid (or its salt) or copolymer of acrylic acid (or its salt). The cellulose ether is methyl cellulose, hydroxypropyl cellulose, hydroxypropylmethyl cellulose or their mixture.

U.S. Pat. No. 4,292,303 is a transdermal delivery system of clonidine in a matrix comprising a polar plasticizer, such as polyethylene glycol, or a mixture of glycerol and polyethylene glycol, and with polyvinylalcohol and a water-soluble polymer such as an agar, gum arabic, gum tragacanth, polyacrylic acid, polymethacrylic acid, polyvinyloxazolidone, polyvinylmorpholinone, and polyvinylpiperidonepolyvinylpyrrolidone. Polyalkylene glycols such as polyethylene glycol and polypropylene glycol may replace all or part of the glycerol.

US 2009-0028929 describes a transdermal patch containing nitroglycerine and a matrix layer comprising: nitroglycerin, acrylic acid/2-ethyl-acrylate/methyl-acrylate copolymer, sorbitan monooleate, propylene glycol and optionally excipients.

WO 1996/023463 relates to a transdermal patch for treating Alzheimers Disease containing xanomeline, azone, ethanol, water, propylene glycol, and gelling agent, such as Klucel HF.

There is a need for a composition which provides higher dermis concentrations of active agents and would therefore increase its therapeutic benefits in the treatment of skin conditions. The embodiments of this invention provide an improvement over traditional patches and topical products utilized to deliver medications.

SUMMARY OF THE INVENTION

The present invention is an occlusive dressing comprising (a) an elastomeric gel and (b) one or more active agents, said elastomeric gel comprising a plasticizing oil phase and a block copolymer agent.

In a preferred embodiment, the block copolymer is selected from styrene ethylene butylene styrene block copolymer (SEBS) and styrene ethylene propylene styrene block copolymer (SEPS).

In another preferred embodiment, the plasticizing oil is selected from one or more mineral oil, synthetic oil, petrolatum naphthenic oil, synthetic polybutene, and synthetic polypropylene.

Elastomeric gels of the invention are preferably formed by mixtures of 5% to 9% by weight of block copolymer and 90% to 95% by weight of plasticizing oil.

In another embodiment, the invention comprises 0.5% to about 50% by weight of active agent. In preferred formulations, the active agent is apolar. In other preferred formulations, the active agent is aprotic.

In some embodiments, the active agent is impregnated in the plasticizing oil phase.

In some embodiments, the active agent is impregnated in the block copolymer phase.

In still other embodiments, the active agent is impregnated in both the plasticizing oil phase and in the block copolymer phase.

Without being bound to any particular theory, it is believed that the active agent shifts from the occlusive dressing to the subject on which it is applied at temperature ranges from 35° C. to 37° C.

In some embodiments, the active agent shifts from the occlusive dressing into the epidermis layer. In other embodiments, the active agent shifts from the occlusive dressing into the epidermis layer. In still other embodiments, the active agent shifts from the occlusive dressing into the subcutaneous dermal layer.

Active agents include one or more antibiotic, steroid, antiviral and antifungal and pharmaceutically acceptable salts thereof, pharmaceutically acceptable analogs thereof, and any combination of any of the foregoing.

The invention also relates to a method of treatment of a fungal infection of the dermis of a subject, said method comprising applying an occlusive dressing comprising (a) an elastomeric gel and (b) one or more active agents, said elastomeric gel comprising a plasticizing oil phase and a block copolymer agent to the affected area or areas of said subject.

Fungal infections capable of treatment with the occlusive dressing of this invention include *Candida* sp.

The invention also relates to a method of treatment of a bacterial infection of the dermis of a subject, said method comprising applying an occlusive dressing comprising (a) an elastomeric gel and (b) one or more active agents, said elastomeric gel comprising a plasticizing oil phase and a block copolymer agent to the affected area or areas of said subject.

Bacterial infections capable of treatment with the occlusive dressing of this invention include MRSA and MRSE.

The invention also relates to a method of treatment of a viral infection of the dermis of a subject, said method comprising applying an occlusive dressing comprising (a) an elastomeric gel and (b) one or more active agents, said elastomeric gel comprising a plasticizing oil phase and a block copolymer agent to the affected area or areas of said subject.

Viral infections capable of treatment with the occlusive dressing of this invention include HIV, HPV, Herpes Simplex-I and Herpes Simplex-II.

The methods of treatment apply to subjects such as a mammal. Preferably, the mammal is a human.

The invention also relates to a method of making the occlusive dressing said method comprising blending one or more medications, a plasticizing oil and a block copolymer. In a preferred method of making the occlusive dressing, said method consists of molding or extruding said dressing. The occlusive dressing is selected from a vessel, a glove, a sock, a gauze, a suppository/ovule, a foam, an ointment, a cream, a spray and a volatile liquid.

The invention also is directed to a method of preventing, treating, curing or mitigating an infectious disease utilizing an occlusive dressing comprising (a) an elastomeric gel and (b) one or more active agents, said elastomeric gel comprising a plasticizing oil phase and a block copolymer agent, wherein said infectious disease is selected from one or more: dermatitis and other eczematous disorders, mastocytosis, vernal deratoconjunctivitis, vernal conjunctivitis, vernal keratitis, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, urethritis herpes labialis, actinic keratosis, staphylococcal infections, MRSA, MRSE, herpes simplex virus-I, herpes simplex virus-II, rheumatoid arthritis, omychomycosis, vaginitis and/or bacterial vaginosis, trichomonas, Gardnerella, HPV, *Candida* species, Chlamydia, HIV-AIDS and epithelial precancerous lesion.

In a preferred embodiment, the occlusive dressing of comprises 99.5% to 98% elastomeric gel compound and 0.5 to 2% clotrimazole. The present invention is a topical composition comprising (a) at least one elastomeric gel compound and (b) an active agent component selected from Clotrimazole, ketaconazole, econazole, miconazole and spectazole and pharmaceutically acceptable salts thereof, pharmaceutically acceptable analogs thereof, and any combination of any of the foregoing. Suitable salts of the invention are known to those skilled in the art.

In one embodiment of the invention, the composition includes an effective amount of the clotrimazole component and at least one elastomeric gel compound to treat or prevent the onset of a skin condition The elastomeric gel compound improves the retention of the active agent component in the dermis. For instance, the topical composition including an elastomeric gel compound can yield higher dermis-layer concentrations of the active agent component over 8 and 48 hours after a single administration than a similar topical composition without the elastomeric gel compound.

Also provided is a topical unit dosage form comprising the composition of the present invention. The topical unit dosage form will optionally include a physiologically acceptable vehicle. For example, the topical composition or unit dosage form of the present invention can be an aqueous, semi-aqueous and/or oil-based solution or suspension. Suitable vehicles include, but are not limited to, water, isopropylmyristate (IPM), and polyethylene glycol (PEG) and water solutions. The topical composition or unit dosage form may be, for example, in the form of a cream, a gel, a lotion, an ointment, a suspension, or an emulsion (e.g. an oil-in-water emulsion).

Another embodiment is a method for administering a clotrimazole component, an analogue thereof, or a mixture thereof to an animal (e.g., a patient) in need thereof, by topically administering the composition or dosage unit form (s) of the present invention to the animal.

Yet another embodiment is a method of preventing, treating, curing or mitigating skin conditions, including but not limited to, dermatitis and other eczematous disorders, mastocytosis, vernal deratoconjunctivitis, vernal conjunctivitis, vernal keratitis, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, urethritis herpes labialis, actinic keratosis, staphylococcal infections, MRSA, MRSE, herpes simplex virus-I, herpes simplex virus-II, rheumatoid arthritis, omychomycosis, vaginitis and/or bacterial vaginosis, trichomonas, Gardnerella, HPV, *Candida* species, Chlamydia, HIV-AIDS and epithelial precancerous lesion in an animal in need thereof (e.g., a patient) by administering an effective amount of the composition or dosage unit form(s) of the present invention to the animal. Yet another embodiment is a method of preparing a composition of the present invention by mixing at least one delivery agent compound and at least one active agent component.

Yet another embodiment is a method of reducing the transmission of sexually-transmitted diseases (STDs).

DESCRIPTION OF THE PREFERRED EMBODIMENTS

The composition of the present invention comprises one or more elastomeric gel compounds of the present invention and/or one or more active agent (e.g. Clotrimazole, ketaconazole, econazole, miconazole and spectazole) component. The elastomeric gel compound and active agent component are typically mixed prior to administration to form an administration composition (which may comprise a unit dosage form).

The administration composition may also contain other active ingredients such as anti-allergic medications (e.g. oxatamide, cromolyn, diphenhydramile, loratidine, deslora-tidine, fexophenadine, montelukast), glucocorticoids or corticosteroids (e.g. betamethasone valerate, triamcinolone acetonide, clobetasone butyrate, hydrocortisone and triamcinolone).

The administration composition may also contain other ingredients known to provide therapeutic effects to skin. These ingredients include, but are not limited to, aloe, antioxidants, moisturizers or humectants, vitamins, surfactants, hydroxy acids, proteolytic enzymes, skin lightening agents (e.g. melanin inhibitors, melanin bleaches), sunscreen, colorants, perfumes, preservatives, pigments, antiseptic agents, and toners. Any of the ingredients listed in the *International Cosmetic Ingredient Dictionary and Handbook*, 9$^{th}$ Ed. 2002, by The Cosmetic Toiletry Fragrance Association (ISBN 1882621298), which is hereby incorporated by reference in its entirety, may be incorporated into the administration composition of the present invention.

The administration composition is typically applied topically to a targeted area of skin. The administration composition may be applied daily, for typically at least several days. However, more frequent application is also contemplated. For example, in the treatment of injured tissue, such as a rash, or an allergy-induced skin problem, it may be desirable to continuously maintain the administration composition on the affected area during healing, with applications of the administration composition from two to four times a day or more frequently. In a preferred embodiment, the application is only necessary once or twice daily, due to the adhesive nature of the elastomeric gel disclosed herein. Use may also be for extended periods, including years.

The amount of the active component in the administration composition is an effective amount of active component, which can be determined by those skilled in the art depending on the condition for which it is administered. The unit dosage form may comprise, for example, from about 0.01% to 10%, or about 0.01% to about 7%, or about 0.5% to about 4.0% of the active agent component (e.g. clotrimazole, ketaconazole, econazole, and miconazole). In alternative embodiments, an active agent component is added until the administration composition is saturated with the active agent compound.

The present invention provides, in addition to compositions as described above, a method for improving skin conditions. The method comprises applying the topical composition to an affected area to treat, cure or mitigate one or more: dermatitis and other eczematous disorders, mastocytosis, vernal deratoconjunctivitis, vernal conjunctivitis, vernal keratitis, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, urethritis herpes labialis, actinic keratosis, staphylococcal infections, MRSA, MRSE, herpes simplex virus-I, herpes simplex virus-II, rheumatoid arthritis, omychomycosis, vaginitis and/or bacterial vaginosis, trichomonas, Gardnerella, Human Pappiloma Virus (HPV), *Candida* species, Chlamydia, HIV-AIDS and epithelial precancerous lesion in an animal in need thereof (e.g., a patient) by administering an effective amount of the composition or dosage unit form(s) of the present invention to the animal. The term "Active agent" or "medication" as used herein refers to a substance used to alter the biological function of fungus, bacteria, virus or human, and for administration to a mammal, including a human, which when administered to said mammal is intended to treat, cure or mitigate a disease. The diseases of this invention are preferably infectious diseases chosen from fungus, bacteria and viruses. A preferred infection to treat, cure or mitigate is *Candida* species, such as *albicans*. Limiting examples are active agents which are antifungals chosen from: Clotrimazole, ketaconazole, econazole, miconazole, spectazole; Sertaconazole, INN of 1-[2-[(7-Chlorobenzo[b]thien-3-yl)methoxy]-2-(2,4-dichlorophenyl) ethyl]-1H-imidazole and CAS REG No. 99592-32-2 is a useful antifungal gent for treatment of diseases caused by fungi and yeasts in man and in animals. Sertaconazole, as well as its pharmaceutically acceptable addition salts, is disclosed in EP 0151477. The R-(−)-enantiomer of sertaconazole is disclosed in PCT application WO 03/68770 as well as its pharmaceutically acceptable addition salts.

Natural antifungal mixtures such as those disclosed in U.S. Pat. No. 7,429,396 include mixtures of plant materials comprising *Origanum vulgare* L., *Thymus vulgaris* L., *Rosmarinus officinalis* L., and *Lavandula officinalis* L., *Cinnamomum zeylanicum* Nees and *Hydrastis canadensis* L.

Other antifungals are listed in International Patent Application No. WO/2009/048841, as well as in Table I, herein.

Limiting examples are also active agents which are antibacterials chosen from:

Metronidazole, vancomycin, lincomycin, clindamycin, erythromycin, ceftiraxone, azithromycin, doxycycline Limiting examples are also active agents which are antivirals chosen from:

Acyclovir, valacyclovir, azathioprine (AZT).

The term "Apolar" or "Non-polar" as used herein refers to substance wherein there is an equal sharing of electrons between two different atoms. Limiting example of apolar molecules include diatomic molecules of the same element and most carbon-containing compounds.

The term "Aprotic" as used herein refers to a substance that cannot donate a hydrogen (i.e. is not hydrogen binding), is not acidic and has the ability to stabilize ions. Limiting examples are dimethyl sulfoxide, dimethyl formamide, dioxane, hexamethylphosphorotriamide and tetrahydrofuran.

The term "Elastomeric gel" or "Elastomeric Agent" or "Elastomeric Compound" as used herein refers to a gelatinous substance formed by mixtures of various amounts of one or more plasticizing oils, with admixtures of one or more block copolymers, such as SEBS and SEPS. Preferred elastomeric gels of the invention are located in U.S. Pat. Nos. 4,369,284, 4,618,213, 5,153,254, 5,262,468, 5,334,649, 5,336,708, 5,466,232, 5, 806,523, 5,807,360 and 5,782,818 which are incorporated in their entirety herein.

The term "Methacillin resistant *Staphylococcus aureus*" or "MRSA" as used herein refers to a species of *Staphylococcus*

*aureus* which continues to grow and multiply on or within its host despite treatment with many conventional antibiotics, except vancomycin.

The term "Methacillin resistant *Staphylococcus epidermidis*" or "MRSE" as used herein refers to a species of *Staphylococcus epidermidis* which continues to grow and multiply on or within its host despite treatment with many conventional antibiotics, except vancomycin.

The term "Occlusive Dressing"—as used herein refers to an agent for delivery of an active agent comprising one or more active agents and an elastomeric gel.

The term "Plasticizing oil" or "Plasticizing Agents"—as used herein refers to dispersants which are additives that increase the fluidity of the material to which they are added. Limiting examples of plasticizing oils useful in this invention are disclosed in U.S. Pat. No. 5,807,360 which is incorporated in its entirety herein. These include mineral oil, naphthenic oils and Synthetic oils such as Shellflex 371, petroleum paraffinic oils, petroleum naphthenic oils, synthetic polybutene oils, synthetic polypropene oils, synthetic polyterpene oils, and mixtures thereof. Other plasticizing agents useful in this invention include triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, alkyl sulphonic acid phenyl ester and mixtures thereof.

The term "Polystyrene-ethylene-butylene-styrene" or "SEBS" as used herein is a block copolymer having styrene endblock to ethylene and butylene center block.

The term "Polystyrene-ethylene-propylene-styrene" or "SEPS" as used herein is a block copolymer having styrene endblock to ethylene and propylene center block.

The term "Skin" or "dermis" as used herein refers one or more of the layers of skin in a human, including the epidermis, the dermis and the subcutaneous dermal layers.

The term "effective amount of the pharmaceutical formulation" as used herein is an amount of the pharmaceutical formulation described which is effective to treat, cure, mitigate or prevent a condition in a subject to whom it is administered over some period of time, e.g., provides a therapeutic effect during a desired dosing interval. Generally, an effective amount of the pharmaceutical formulation includes amounts of active ingredient and an elastomeric gel to treat or prevent the desired condition over a desired period of time (i.e., an effective amount of elastomeric gel and an effective amount of active agent).

The term "treat" or "treatment" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, including for example, infectious diseases; or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

The terms "sustained release" "extended release" or "long acting" as used herein refers to the release of an active ingredient over an extended period of time leading to lower peak plasma concentrations and a prolonged $T_{max}$ as compared to "immediate release" or "regular release" formulations of the same active ingredient.

The term "bioavailability" refers to the rate and extent to which the active ingredient (active agent, e.g Clotrimazole, ketaconazole, econazole, miconazole spectazole) or active moiety is absorbed from a drug product and becomes systematically available.

Active Agents

Active agents which may be employed are those which are pharmaceutically acceptable including salts, isomers and prodrugs of the active agents disclosed herein. A preferred active agent is clotrimazole. Other active agents useful in this invention are listed in Table I.

In one embodiment, the pharmaceutical formulation includes from about 5 to about 60 milligrams of active agent/gram of final topical product. In yet another embodiment, the pharmaceutical formulation provides 2.5, 5, 10, 20, 30 40, or 60 milligrams of active agent per gram of topical product. In yet another embodiment, the pharmaceutical formulation includes about 2.5, 5, 10, or 20 milligrams of active agent per gram of active product. Other amounts of active agents will present themselves to those of ordinary skill in the art.

Active agents of this invention include, but are not limited to those listed in Table I.

TABLE I

Acyclovir
AZT
Azithromycin
Benzoil peroxide
Ceftriaxone
Clindamycin
Clotrimazole
Doxycycline
Erythromycin
Fluconazole
Itrazonazole
Metronidazole
Nystatin
Povidone iodine
Sertaconazole
Silver Sulfadiazene
Sulfasalazine
Trimethoprim/Sulfamethoxazole
Tolnaftate Delivery Systems The pharmaceutical formulations may be in the form of a liquid, volatile solution, suspension, gel or semi-solid. Liquid formulations may be water-based. Dosing solutions may be prepared by mixing a solution of the elastomeric gel with a solution of active agent prior to administration. Alternately, a solution of the elastomeric gel may be mixed with the solid form of the active agent. The elastomeric gel and the active agent may also be mixed as dry powders and then dissolved in solution. Stabilizing additives may be incorporated into the solution, at, for example, a concentration ranging between about 0.1 and 20% (w/v). The solution may also include a pharmaceutically acceptable carrier, such as phosphate buffered saline and citrate buffers. Other suitable additives include sodium chloride and dextrose.

The pharmaceutical formulations can include any one or combination of excipients, diluents, disintegrants, lubricants, fillers, plasticizers, colorants, flavorants, taste-masking agents, sugars, sweeteners, salts, and dosing vehicles, including, but not limited to, water, 1,2-propane diol, ethanol, olive oil, or any combination thereof.

The amount of active agent (e.g. Clotrimazole, ketaconazole, econazole, miconazole and spectazole) included in the pharmaceutical formulation is an amount effective to accomplish the purpose of the active agent for the target indication. The amount of active agent in the pharmaceutical formulation typically is a pharmacologically, biologically, therapeutically, or chemically effective amount. However, the amount can be less than that amount when the pharmaceutical formulation is used in a dosage unit form of the present invention because the dosage unit form may contain a plurality of elastomeric gel/active agent pharmaceutical formulations or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the pharmaceutical formulations of the invention may deliver active agents more efficiently than formulations containing the active agent alone, lower amounts of active agent than those used in prior dosage unit forms or delivery systems can be administered to the subject, while still achieving the same blood levels and/or therapeutic effects.

The elastomeric gels facilitate the delivery of active agents, particularly in topical form, but are also useful in intranasal, sublingual, intraduodenal, subcutaneous, buccal, intracolonic, rectal, vaginal, mucosal, pulmonary, transdermal, intradermal, parenteral, intravenous, intramuscular and ocular systems.

The pharmaceutical formulation can be a sustained release pharmaceutical formulation which provides for controlled, modified, delayed and/or sustained release of the active agent. Such formulations can be prepared by methods known in the art. In particular, topical formulations with the elastomeric gel described herein create high surface area contact points to bring the individual to cure. The topical formulation creates a thin film science and chemistry to change the environment for recurring disease, breaking the cycle of infection and reinfection of infectious diseases and effectuating a cure.

Topical preformed agents of the invention may be produced by polymeric molding into any desired shape to conform to specific areas of the anatomy which may become infected with an infectious agent. For example, an occlusive dressing may be formed and applied to one or more affected areas.

The extrusion process is one in which the molten polymers is forced through a shaped orifice, and the extrudate is then cooled, usually until solid. The cross section of the extrudate (perpendicular to the flow direction) usually has the same shape as the orifice. Due to the importance of extrusion commercially, improved dies are constantly being sought, so that the process runs more cheaply, and/or with less off-quality production, etc. A particular problem in this process is "die drips", which are small portions of (usually) molten polymer which collect around the die orifice, and which can cause problems of product defects and downtime. United States Patent Application 20030213189 discloses methods for bending preformed thermoplastic extrusions having at least one cavity and filling at least one of the extrusion cavities with polymer foam and curing the foam within the filled cavity. U.S. Pat. No. 6,659,020 relates to an apparatus and method of producing an elongate calibrated extrusion of a formable material. U.S. Pat. No. 4,822,546 describes a polymer extrusion die which is advantageous for use with high flow polymers. U.S. Pat. No. 4,618,213 describes various proportions of block copolymer and plasticizing oil, and methods of extrusion, utilization of dies, or making sheets or lenses of the material. International Patent Application WO/1995/024303 discloses an improved die, containing one or more orifices, for the extrusion of polymers is disclosed wherein the orifices are flared at the polymer discharge end, and the orifices have certain relative dimensions and configurations. The dies are useful for producing items such as films, shaped profiles, sheets, fibers, strands, etc. Also disclosed are a process for using the die, and an extrusion apparatus containing such a die. Non-limiting examples of shapes include vessels, gloves, socks and gauzes. In the alternative, application may be via one or more patches or via a gel or other topical formulation (e.g. liquid, solution, suspension, cream, etc.) by which the patient may spread a thin layer over affected areas. U.S. Pat. Nos. 6,659,020, 4,618,213, 4,822,546 and International Patent Application WO/1995/024303 are incorporated herein by reference in their entirety. Other methods and machinery useful for the production of extrusions and films of this invention known to those in the art, may also be utilized in this invention.

The preferred embodiment of the invention is an elastomeric gel comprising one or more block copolymers and an active agent selected from Table I.

In another preferred embodiment of the invention an elastomeric gel comprising one or more block copolymers and an active agent selected from agents disclosed herein, and delivers the active agent into the dermis. In another embodiment, the active agent shifts from the occlusive dressing to the dermis of the subject on which it is applied at temperature ranges of about 35 degrees Celsius to about 37 degrees Celsius.

The pharmaceutical formulations are useful for administering active agents to mammals including, but not limited to, horses, rodents, cows, pigs, dogs, cats, primates, and particularly humans.

According to another embodiment the pharmaceutical formulation includes other medications which treat, cure, mitigate or prevent infectious diseases or other indications for which active agents disclosed herein are effective. For example, in one embodiment, the pharmaceutical composition includes a steroidal agent. In another embodiment, the pharmaceutical composition includes an adjunctive agent. The pharmaceutical formulation of the present invention may be administered during or subsequent to the adjunctive agent. According to one preferred embodiment, when the pharmaceutical formulation is to be administered concomitantly, the pharmaceutical formulation includes an adjunctive topical agent, such as a steroid.

Preparation of Elastomeric Gels

The elastomeric gels of the invention may be prepared by methods known in the art. For example, as formulas disclosed in U.S. Pat. Nos. 4,369,284, 4,618,213, 5,153,254, 5,262,468, 5,334,649, 5,336,708, 5,466,232, 5, 806,523, 5,807,360 and 5,782,818 which are incorporated herein by reference in their entirety.

Preferred elastomeric gels are formed by mixtures of 5% to 9% by weight of block copolymer and 90% to 95% by weight of plasticizing oil, and trace amounts of adjunctive agents, such as pigments and fillers.

The active agents may be added to the elastomeric gel mixture at any time using any method. For instance, the active agents may be added with the other components and thus before extrusion; they may be added after extrusion; or they may be added through a port at the time of use.

Preferably, the active agents are added to the elastomeric gel mixture prior to extrusion to the preferred shape or placement into a mold or feeding through an extrusion machine.

Alternately, the active agents may be added after extrusion if they are temperature sensitive. One or more agents may be added before extrusion, and others may be added after extrusion, or all may be added before or all may be added after extrusion.

The active agents may not necessarily be added before extrusion, but instead may be dissolved or delivered mechanically by warming action through a physical port, using a method similar to that of delivering an enema. The active agent could possibly be dissolved in an optimized polymeric mixture, or the active agent could be delivered through a polymer that has openings suitable to allow the agent through, similar to a Swiss cheese pattern, or a permeation tube.

Methods of Treatment

The pharmaceutical formulation of the present invention can be administered to treat and/or prevent any disorder for which the active agents are known to be capable of treating and/or preventing. Typically, an effective amount of the pharmaceutical formulation is administered to treat and/or prevent the desired disorder. Such disorders include, but are not limited to, dermatitis and other eczematous disorders, mastocytosis, vernal deratoconjunctivitis, vernal conjunctivitis, vernal keratitis, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, urethritis herpes labialis, actinic keratosis, staphylococcal infections, herpes simplex virus-I, herpes simplex virus-II, rheumatoid arthritis, omychomycosis, vaginitis and/or bacterial vaginosis, trichomonas, Gardnerella, HIV, HPV, Chlamydia. *Candida* species, Chlamydia, HIV-AIDS, epithelial precancerous lesion, and other indications which are treatable with active agents, such as those described herein.

Generally in man, a daily topical dosage of active ingredient will be from about 5 milligrams to about 50 milligrams per application, although lower and higher amounts can be used. The active ingredient, the drug, can be employed in useful compositions according to the present invention in such dosage forms as solution, semisolid and solid form. These dosage forms preferably deliver from about 5 milligrams to about 50 milligrams of active ingredient per application, with a range from about 10 milligrams to about 25 milligrams per application being preferred.

The pharmaceutical formulations can be administered to treat the indications for active agents found in (1) the *Physicians' Desk Reference* (58$^{th}$ Ed., 2004, Medical Economics Company, Inc., Montvale, N.J.), (2) Fauci, A S, et. al., *Harrison's Principles of Internal Medicine* (14$^{th}$ Ed., 1998, McGraw-Hill Health Professions Division, New York. All of the above-mentioned patents and publications are herein incorporated by reference in their entirety.

The following prophetic examples illustrate the invention without limitation. All parts are given by weight unless otherwise indicated.

Alternate Embodiments

A formulation may contain one to four polymers and copolymers combinations varying in percentages of each from 0-100%, with a preferred ratio of 25% each of the four polymers. The hydrophobic oil can be either an active ingredient in the oil as a carrier or the oil itself could have antiseptic properties. The percentages of the hydrophobic medicinal oil would vary from 0-99%.

An example would be SEBS copolymers and SEPS block copolymers in a polymer ratio of 1:5 to 5:1 with 1:1 being preferred. Particularly are gels formed from 5-9 wt % of the block copolymer admixture and 90-94% by weight of the plasticizing oil. However, if you add trimixtures, this level changes. The relative percentages are such to create an optimal situation so that the elected oil as a carrier vs. oil as antimicrobial agent (ie. antifungal) if target is against *Candida* species (aka yeast infections) would have a rate of kill if subject were to use the device minimum of once per day to be effective but ten times per day to not become toxic. This optimal delivery system is highly dependent on the agent chosen, carrier oil of choice as well as the mixture of polymers.

Certain other potential compounds that could also be "x"-azoles type antifungals (imidazole, triazole, and thiazole antifungals) as well as poly-"ene" antimycotics include but are not limited to, Miconazole, Ketoconazole, Clotrimazole, Econazole, Omoconazole, Bifonazole, Butoconazole, Fenticonazole, Isoconazole, Oxiconazole, Sertaconazole, Sulconazole, and Tioconazole.

Other compounds, such as Undecylenic Acid and compounds from its class, could also be useful as an additive.

Prophetic Example 1

Human Cadaver Skin Model and Dosing

The in vitro human cadaver skin model has proven to be a valuable tool for the study of percutaneous absorption and the determination of the pharmacokinetics of topically applied excipients and/or drugs. The model uses human cadaver skin mounted in specially designed diffusion chambers which allow the skin to be maintained at a temperature and humidity that match typical in vivo conditions (See Franz, Percutaneous absorption: On the Relevance of in vitro data, *J Invest Derm.*, 64:190-195 (1975)). Typically a finite dose of formulation is applied to the outer surface of the skin and absorption of the compound of interest is measured by monitoring its rate of appearance in the receptor solution bathing the inner surface of the skin. Data defining total absorption, rate of absorption, as well as skin content can be accurately determined in this model. The method has historic precedent for accurately predicting in vivo percutaneous absorption kinetics (See Franz T. J., Skin: Drug Application and Evaluation of Environmental Hazards, *Current Problems in Dermatology*, 7:58-68 (1978). Human cadaver obtained within 24 hours of death, or surgically excised trunk skin without obvious signs of skin disease were used in these examples. Skin was cleared of subcutaneous tissue and approximately 50% of the dermis by scalpel. As received, the skin is sealed in a water-impermeable plastic bag, having been shipped on wet ice. If not used on the day of arrival, the skin was stored at less than −70° C. until the day of the experiment. Prior to use it was thawed by placing the bag in ~37° C. water, then rinsed in tap water to remove any adherent blood or other material from the surface. Skin from a single donor was cut into multiple smaller sections large enough to fit onto 0.8 cm$^2$ Franz diffusion cells (Crown Glass Co., Somerville, N.J.). Skin thickness was measured and recorded. The receptor chamber was filled to capacity with a receptor solution of phosphate-buffered isotonic saline (PBS), pH 7.4±0.1, and the donor chamber was left open to the ambient laboratory environment. The cells were then placed in a diffusion apparatus in which the receptor solution is stirred magnetically at ~600 RPM and which is maintained to achieve a skin surface temperature of 33.0±1.0° C. Skin surface temperatures from representative chambers were measured and recorded. To assure the integrity of each skin section, its permeability to tritiated water was determined before application of the test products (See Franz T. J., The use of water permeability as a means of validation for skin integrity in in vitro percutaneous absorption studies, *Abst. J Invest Dermatol.* 94:525 (1990)) Following a brief (0.5-1 hour) equilibrium period, $^3H_2O$ (NEN, Boston, Mass., sp. Act. ~0.5 µCi/mL) was layered across the top of the skin by dropper so that the entire exposed surface was covered (approximately 100-150 µL). After 5 minutes the $^3H_2O$ aqueous layer was removed. At 30 minutes the receptor solution was collected and analyzed for radioactive content by liquid scintillation counting. Skin specimens in which absorption of $^3H_2O$ was less than 1.25 µL-equ were considered acceptable.

Prior to administration of the topical test formulations to the skin sections, the receptor solution was replaced with fresh Phosphate Buffered Saline (PBS) solution prior to dosing. All formulations were then applied to the skin sections using a positive displacement pipette set to deliver 5 µL (5 µL/0.8 cm$^2$). The dose was spread throughout the surface with the Teflon tip of the pipette. Five to ten minutes after application the chimney portion of the Franz Cell was replaced.

This model was used to prophetically model dosing and conditions for the present invention.

Prophetic Example II

Gels will be prepared utilizing several methods with the following general formulation:

| Component | Amount (%) |
|---|---|
| SEBS | 5-9 |
| SEPS | 5-9 |
| Plasticizing oil | 90-95 |
| Active Agent | 0.001-5 |

Prophetic Example III

Gels will be prepared using the following general formulation:

| Component | Amount (%) by weight |
|---|---|
| Elastomeric Gel Compounds | 99.5 to 98% |
| Clotrimazole | 0.5 to 2.0% |

Clotrimazole (1 g) will be dissolved in elastomeric compound at about 70° C. to 80° C. to give a uniform gel and to make a total of 5 grams. After stirring well, the mixture will be cooled to give a transparent gel preparation. Sheets or pellets of the material will be placed in extruder to produce vessel-shaped material containing the active agent, clotrimazole.

Prophetic Example IV

Test Formulations and Analytical Methods

A. Sample containing known organisms (*Candida* sp., et. al.) will be swabbed with sterile saline moistened swabs and plated in Potato Dextrose Media (PDM). Plates will be incubated at 30° C. to 40° C. and examined for fungal or bacterial or viral growth daily for 14 days. Also, samples swabbed with sterile saline moistened swabs will be placed in 1.0 ml of Phosphate Buffered Saline (PBS) with 10% Methanol.

B. Inoculation of samples: Samples will then be inoculated with known control organisms i.e. *Candida*.

All fungal organisms will initially be cultured on PDM for 14 days prior to diluting in sterile distilled water. An inocula from the PDM will be taken and placed in 3 cc. of sterile distilled water. Each inocula will then be counted using a hemocytometer and inoculums will be adjusted to approximately 155 spores/ml. The final dilution (155 spores/ml) will be labeled as neat or undiluted. Specimens will then be diluted in a 1:10 dilution to a final concentration of 1:10$_5$ organisms/ml. Each dilution for each organism will be diluted with the final concentration being:

1. Neat (undiluted)—155 spores/ml
2. 1:10—15.5 spores/ml
3. 1:100—1.55 spores/ml
4. 1:1000—0.155 spores/ml
5. 1:10000 (10$_5$)—<0.1 spores/ml The polymeric elastomeric gel premixed with Exhibit A chemistry will be added into the presence of the solutions described in 1-5 to eliminate organisms. Optimal list of Exhibit A chemistry will be screened for the lowest cost; return on treatment will be determined and finalized.

Exhibit A chemistry optimized will be transferred to Exhibit B. Exhibit B will then be heated to high temperatures maintained at 50° C., 60° C., or 75° C. for 5 hours as a stress test. The chemistry from Exhibit B will then be repeated and added into the polymeric elastomeric gel and mixed thoroughly. The final film will be placed in the presence of organisms concentrations described in 1-5.

Qualifying Exhibit B chemistries will be separated from failed chemistries and success will be labeled Exhibit C. The final result will be that we have optimized chemistries against 1-5 concentration spore levels for *Candida* sp. that will sufficiently survive high temperature treatments during processing. Samples will be placed in the incubator and evaluated weekly for a total of four weeks. Samples treated with Exhibit C chemistries will show undetectable levels of *Candida* sp. High growth mediums such as PDM when exposed to the polymeric elastomeric gel will not show signs of growth. Such chemistries and their corresponding concentration levels will be determined to be robust for treatment given such conditions mimic human skin conditions.

The above-mentioned patents, applications, test methods, and publications are hereby incorporated by reference in their entirety. Many variations of the present invention will suggest themselves to those skilled in the art in light of the above detailed description. All such obvious variations are within the fully intended scope of the appended claims.

I claim:

1. An occlusive dressing consisting essentially of:

(a) an elastomeric gel consisting of 90 to 95% by weight of a plasticizing oil and 5 to 9% by weight of a block copolymer phase, said block copolymer phase consisting of styrene ethylene butylene styrene block copolymer (SEBS) and styrene ethylene propylene styrene block copolymer (SEPS) in a ratio of 1:1, and (b) one or more active agents selected from the group consisting of antifungal compounds for treating yeast infections caused by *Candida* sp.

2. The occlusive dressing of claim 1 wherein said plasticizing oil is selected from one or more of mineral oil, synthetic oil, petrolatum naphthenic oil, synthetic polybutene, and synthetic polypropylene.

3. The occlusive dressing of claim 1, wherein said dressing comprises 0.5-2% by weight of the active agent, and the active agent is selected from the group consisting of miconazole, ketoconazole, clotrimazole, econazole, omoconazole, bifonazole, butoconazole, fenticonazole, isoconazole, oxiconazole, sertaconazole, sulconazole, and tioconazole.

4. The occlusive dressing of claim 1, wherein the active agent is impregnated in the plasticizing oil phase.

5. The occlusive dressing of claim 1 wherein said active agent is impregnated in the block copolymer phase.

6. The occlusive dressing of claim 1 wherein the active agent shifts from the occlusive dressing to the subject on which it is applied at temperature ranges from 35° C. to 37° C.

7. The occlusive dressing of claim 1 wherein said active agent shifts from the occlusive dressing into the epidermis, the dermis or the subcutaneous dermal layer.

8. The occlusive dressing of claim 1 wherein said occlusive dressing is selected from a vessel, a glove, and a sock.

9. An occlusive dressing consisting essentially of:
   (a) 98 to 99.5% of an elastomeric gel, said gel consisting of 90 to 95% by weight of a plasticizing oil and 5 to 9% by weight of a block copolymer phase, said block copolymer phase consisting of styrene ethylene butylene styrene block copolymer (SEBS) and styrene ethylene propylene styrene block copolymer (SEPS) in a ratio of 1:1; and
   (b) 0.5 to 2% by weight of Clotrimazole dissolved into the elastomeric gel, said dressing having a form of a vessel.

* * * * *